US012733988B2

(12) United States Patent
Ramirez Luna et al.

(10) Patent No.: US 12,733,988 B2
(45) Date of Patent: Sep. 15, 2026

(54) OPHTHALMIC VISUALIZATION USING SPECTRUM-INDEPENDENT IMAGERS, EDGE DETECTION, AND VISIBLE-IR IMAGE MERGING

(71) Applicant: Alcon Inc., Fribourg (CH)

(72) Inventors: Maximiliano Ramirez Luna, Santa Barbara, CA (US); Hillary Schatz, Fort Worth, TX (US); John Park, Irvine, CA (US)

(73) Assignee: Alcon Inc., Fribourg (CH)

( * ) Notice: Subject to any disclaimer, the term of this patent is extended or adjusted under 35 U.S.C. 154(b) by 528 days.

(21) Appl. No.: 18/466,335

(22) Filed: Sep. 13, 2023

(65) Prior Publication Data

US 2024/0164850 A1 May 23, 2024

Related U.S. Application Data

(60) Provisional application No. 63/384,694, filed on Nov. 22, 2022.

(51) Int. Cl.
*A61B 34/20* (2016.01)
*A61B 3/00* (2006.01)
(Continued)

(52) U.S. Cl.
CPC ............ *A61B 34/20* (2016.02); *A61F 2/1662* (2013.01); *G06T 7/13* (2017.01);
(Continued)

(58) Field of Classification Search
CPC ............ A61B 34/20; A61B 2034/2051; A61B 2034/2057; A61B 2034/2065;
(Continued)

(56) References Cited

U.S. PATENT DOCUMENTS 8,836,793 B1 9/2014 Kriesel et al.
2015/0164319 A1* 6/2015 Kim .................... G06V 40/193 351/210

(Continued)

OTHER PUBLICATIONS

PCT International Search Report (ISR) Dated Dec. 15, 23, Int'l Application No. PCT/IB2023/059100.

*Primary Examiner* — Matthew C Bella
*Assistant Examiner* — Shane Wrensford Codrington
(74) *Attorney, Agent, or Firm* — Sanders IP Law

(57) ABSTRACT

A visualization system for an ophthalmic procedure on a target eye, e.g., lens replacement surgery, includes first and second light sources respectively operable for directing visible and NIR light toward the target eye. A hot mirror directs reflected light from the eye along two paths, i.e., a visible light path for reflected visible light and an NIR light path for reflected NIR light. First and second cameras are respectively positioned in the visible and NR light paths to detect the reflected visible or NIR light and output a visible or NIR image. An electronic control unit (ECU) executes a method to detect a perimeter edge of an imaged portion of the target eye in the NIR image using edge detection logic, merges the visible image with the NIR image to construct a combined image, and indicates the perimeter edge in the combined image.

20 Claims, 4 Drawing Sheets

(51) Int. Cl.

| | |
|---|---|
| ***A61B 3/14*** | (2006.01) |
| ***A61B 90/00*** | (2016.01) |
| ***A61F 2/16*** | (2006.01) |
| ***G06T 7/13*** | (2017.01) |

(52) U.S. Cl.
CPC ................. *A61B 2034/2051* (2016.02); *A61B 2034/2057* (2016.02); *A61B 2034/2065* (2016.02); *A61B 2090/364* (2016.02); *A61B 2090/373* (2016.02); *G06T 2207/10048* (2013.01); *G06T 2207/20084* (2013.01); *G06T 2207/20221* (2013.01); *G06T 2207/30041* (2013.01)

(58) Field of Classification Search
CPC ........ A61B 2090/364; A61B 2090/373; A61B 3/0008; A61B 3/14; A61F 2/1662; G06T 7/13; G06T 2207/10048; G06T 2207/20084; G06T 2207/20221; G06T 2207/30041
See application file for complete search history.

(56) References Cited

U.S. PATENT DOCUMENTS

| | | | | |
|---|---|---|---|---|
| 2017/0020627 | A1* | 1/2017 | Tesar ................... | A61B 90/361 |
| 2018/0024341 | A1 | 1/2018 | Romanowski et al. | |
| 2019/0175402 | A1* | 6/2019 | Eil ......................... | G02B 21/20 |

* cited by examiner

OPHTHALMIC VISUALIZATION USING SPECTRUM-INDEPENDENT IMAGERS, EDGE DETECTION, AND VISIBLE-IR IMAGE MERGING

CROSS-REFERENCE TO RELATED APPLICATIONS

The present application claims the benefit of priority to U.S. Provisional Patent Application No. 63/384,694 filed on Nov. 22, 2022, which is hereby incorporated by reference in its entirety.

INTRODUCTION

The present disclosure relates to automated systems and methods for viewing an implantable medical device and surrounding ocular anatomy during an ophthalmic procedure. As appreciated in the art, surgeries of the eye often require an attending surgeon or medical team to illuminate the lens, retina, vitreous, and surrounding tissue within a patient's eye. Visualization of ocular anatomy and possibly of ocular implantable devices is essential in a host of eye surgeries, including but not limited to cataract surgery, refractive lens exchanges (RELs), and other lens replacement procedures.

With respect to lens replacement surgeries in particular, a surgeon first breaks up the patient's natural lens using an ultrasonic probe. After removing the resulting lens fragments through a small corneal incision, the surgeon inserts a replacement lens behind the patient's iris and pupil. The replacement lens, which is referred to in the art as an intraocular lens (IOL), thereafter functions in place of the patient's natural lens. During cataract surgery, a patient's "red reflex", produced by reflection of coaxial light from the retina back to the observer, provides a background with contrast suitable for viewing the patient's natural lens structure and that of the replacement lens. Different microscope and illumination settings will affect the intensity and contrast of the red reflex, with the stability and intensity of the red reflex being a critical property for microscopes during eye surgery.

SUMMARY

Disclosed herein is a system and an accompanying method for automated visualization of a target eye of a patient during an ophthalmic procedure. Ocular implantable devices such as but not limited intraocular lenses (IOLs) can be difficult to view during lens replacement surgeries. Ocular tissue such as the inner limiting membrane (ILM) located between the retina and the vitreous body present similar difficulties. The present solutions disclosed herein are therefore directed to improving a surgeon's ability to visualize ocular implantable devices and ocular anatomy during an ophthalmic procedure, including but not limited to cataract surgeries, refractive lens exchanges (RELs), vitrectomy or other vitreoretinal surgeries, etc.

Current office-based and surgical visualization tools are generally unable to take full advantage of the myriad of potential benefits of infrared (IR) imaging. While this is particularly the case during lens replacement surgeries, it remains true when diagnosing conditions of the eye such as capsular tears or when visualizing similar thin structure such as the above-noted ILM. The human eye is incapable of visualizing light in the IR spectrum. Nevertheless, IR imaging can be used to augment traditional visible spectrum imaging within a suitably equipped surgical suite. In general, the technical solutions described in detail below utilize different image sensors to simultaneously collect two different light path images, and provide a capability for collecting and enhancing image data of specific layers on a patient's ocular lens.

In a possible embodiment, the method starts by irradiating the target eye with separate visible and near IR (NIR) light, i.e., from distinct spectrum-specific light sources. The different spectrums of reflected light from the target eye are directed to similarly distinct wavelength-tuned imagers or cameras. The cameras, which may be embodied as visible and NIR CMOS imagers in one or more embodiments, are configured to detect the visible and NIR spectrums, respectively.

NIR images from the reflected NIR light is processed via edge detection logic of an electronic control unit (ECU) to detect edges in the images, e.g., perimeter edges of an IOL. The ECU combines the visible and NIR images into a combined image, and also outputs a data set describing a corresponding location of the perimeter edge. From this data set the ECU can generate a two-dimensional (2D) or three-dimensional (3D) overlay graphic, which is ultimately superimposed on the combined image in one or more embodiments.

A possible embodiment of the visualization system includes first and second light sources, a hot mirror, first and second complementary metal-oxide-semiconductor (CMOS) image sensors, and an ECU. The first light source in this embodiment is operable for directing visible light toward the target eye, the first light source including an array of red, green, and blue (RGB) laser diodes. The second light source directs NIR light toward the target eye and includes at least one NIR laser diode. The hot mirror is configured to direct reflected light from the target eye along two paths, including a visible light path and an NIR light path. The reflected light includes reflected visible light and reflected NIR light.

As part of this exemplary embodiment, the first CMOS image sensor is positioned in the visible light path, and is configured to detect the reflected visible light and output a visible image comprised of RGB pixels. The second CMOS image sensor is positioned in the NIR light path, and configured to detect the reflected NIR light and output an NIR image comprised of NIR pixels. The ECU is programmed to detect a perimeter edge of an intraocular lens (IOL) in the NIR image using edge detection logic, merge the visible image with the NIR image to construct a combined image, and apply an overlay graphic onto the combined image to indicate the perimeter edge of the IOL.

The visualization system in accordance with another embodiment includes a first light source operable for directing visible light toward the target eye, and a second light source operable for directing NIT light toward the target eye. A hot mirror is configured to direct reflected light from the target eye along two paths, including a visible light path and an NIR light path, wherein the reflected light includes reflected visible light and reflected NIR light. A first camera is positioned in the visible light path, and detects the reflected visible light and output a visible image. A second camera positioned in the NIR light path detects the reflected NIR light and output an NIR image. An electronic control unit (ECU) is programmed to detect a perimeter edge of an imaged portion of the target eye in the NIR image using edge detection logic, merge the visible image with the NIR image to construct a combined image, and indicate the perimeter edge in the combined image.

A method is also disclosed herein for use during an ophthalmic procedure on a target eye. The method may include directing visible light from a first light source toward the target eye, and directing NIR light from a second light source toward the target eye. The method additionally includes directing reflected visible light and reflected NIR light from the target eye along a visible light path and an NIR light path, respectively, using a hot mirror. As part of this exemplary embodiment, the method includes detecting the reflected visible light via a first camera positioned in the visible light path, and outputting a visible image in response thereto, and detecting the reflected NIR light via a second camera positioned in the NIR light path, and outputting an NIR image in response thereto. Additionally, an ECU detects a perimeter edge of an imaged portion of the target eye in the NIR image using edge detection logic, merges the visible image with the NIR image to construct a combined image, and thereafter indicates the perimeter edge in the combined image.

The above-described features and advantages and other possible features and advantages of the present disclosure will be apparent from the following detailed description when taken in connection with the accompanying drawings.

Figure 1:
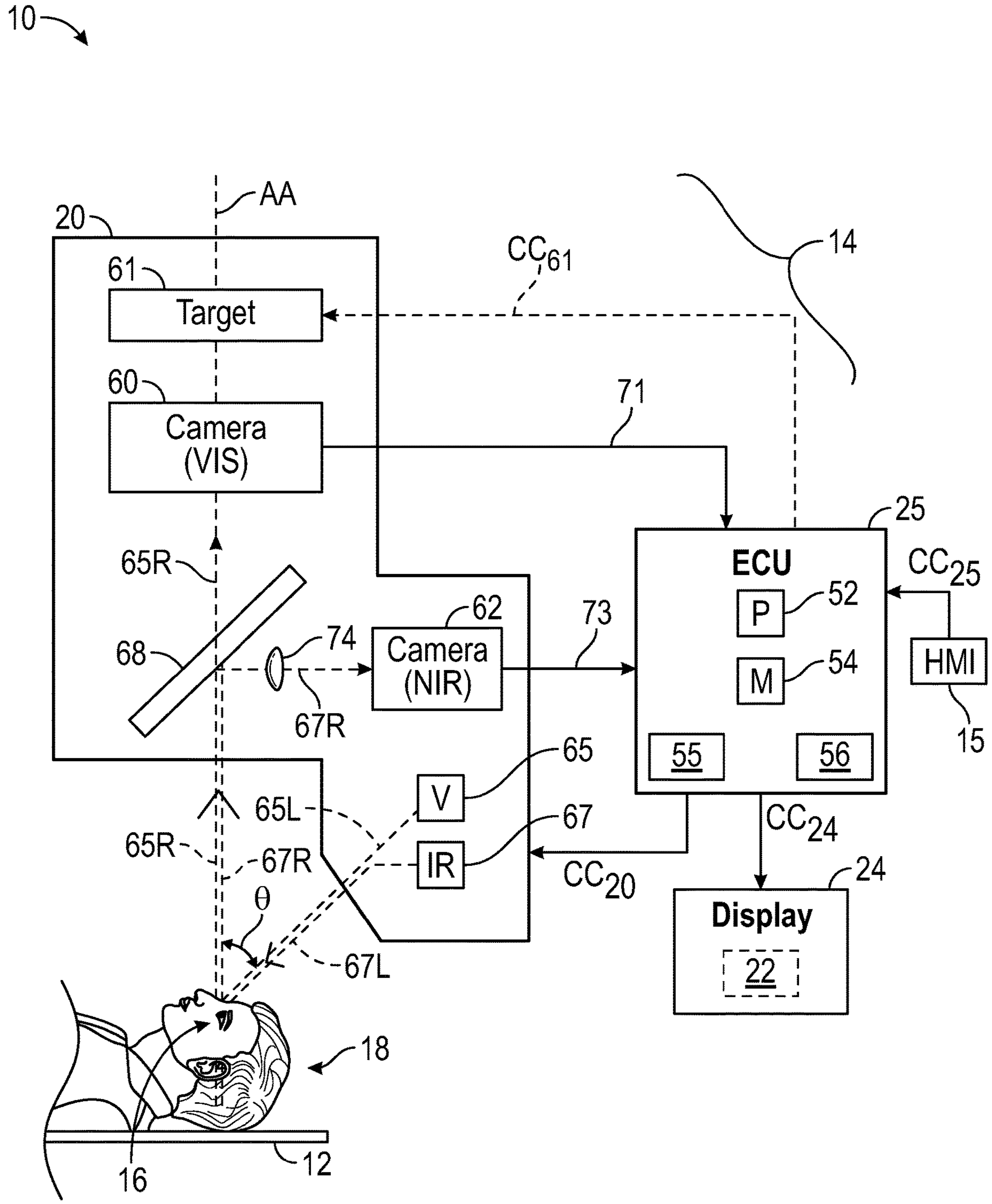
FIG. 1 is a schematic illustration of an exemplary surgical suite configured with a visualization system as set forth in detail herein.

The foregoing and other features of the present disclosure are more fully apparent from the following description and appended claims, taken in conjunction with the accompanying drawings.

DETAILED DESCRIPTION

Embodiments of the present disclosure are described herein. It is to be understood, however, that the disclosed embodiments are merely examples and other embodiments can take various and alternative forms. The figures are not necessarily to scale. Some features could be exaggerated or minimized to show details of particular components. Therefore, specific structural and functional details disclosed herein are not to be interpreted as limiting, but merely as a representative basis for teaching one skilled in the art to variously employ the present disclosure. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Certain terminology may be used in the following description for the purpose of reference only, and thus are not intended to be limiting. For example, terms such as "above" and "below" refer to directions in the drawings to which reference is made. Terms such as "front," "back," "fore," "aft," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

Referring to the drawings, wherein like reference numbers refer to like components, a representative surgical suite 10 is depicted schematically in FIG. 1. The surgical suite 10 may be equipped with a multi-axis surgical robot (not shown), an operating platform 12 such as an adjustable table or chair, and a visualization system 14 configured as set forth herein. The surgical suite 10 can be used when performing a surgical or diagnostic procedure on an eye 16 of a patient 18. The eye 16, being the particular subject surgical site in accordance with the following disclosure, is therefore referred to hereinafter as a target eye 16 for clarity.

As contemplated herein, representative ophthalmic procedures performable in the surgical suite 10 of FIG. 1 include lens replacement surgeries, e.g., cataract surgeries or refractive lens exchanges (RELs), diagnoses or treatments of conditions of the target eye 16 such as capsular tears, or the visualization of the internal limiting membrane (ILM) (not shown) of the target eye 16 or other ocular anatomy. During such procedures, a surgeon may have difficulty visualizing implantable devices and/or the ocular anatomy. While lens replacement surgeries are described in the examples that appear below, those skilled in the art will appreciate that other ophthalmic surgeries or in-office procedures may similarly benefit from the present teachings.

The visualization system 14 shown in FIG. 1 in one or more embodiments may be connected to or in communication with an ophthalmic microscope 20 through which the surgeon is able to view the target eye 16. Alternatively, the visualization system 14 may be partially or fully integrated with the hardware and software of the ophthalmic microscope 20. Using the visualization system 14, the surgeon is able to view one or more combined images 22 of the target eye 16, which may be viewed within the surgical suite 10 via a corresponding high-resolution medical display screen 24, and possibly through ocular pieces (not shown) of the ophthalmic microscope 20.

An electronic control unit (ECU) 25 is also present within the exemplary surgical suite 10 of FIG. 1. The ECU 25, which within the scope of the disclosure is used with or as an integral part of the visualization system 14, is programmed in software and equipped in hardware, i.e., configured, to execute computer readable instructions embodying a method 500, a representative implementation of which is described below with reference to FIG. 5. Execution of the method 500 in turn allows the surgeon to better visualize certain features of the target eye 16 when diagnosing or treating the target eye 16, as noted above.

Figure 2A:
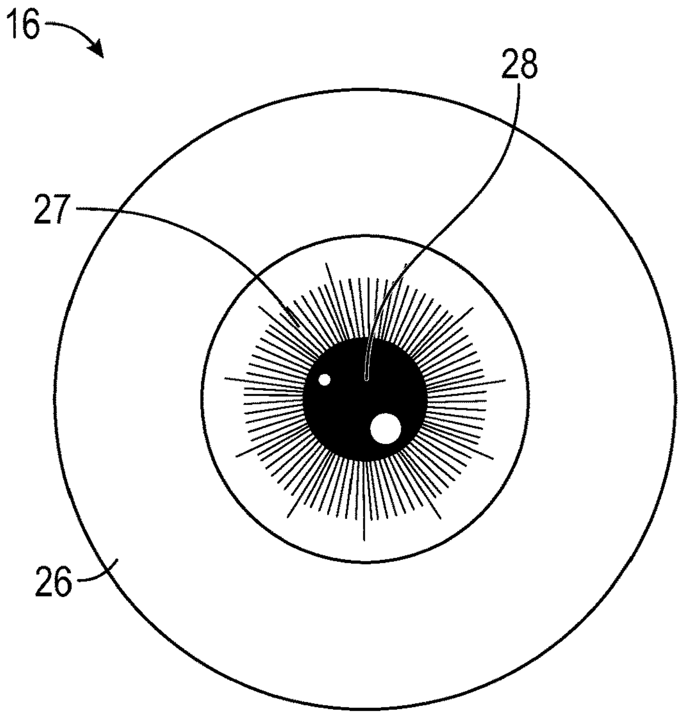
FIG. 2A is a front view illustration of a target eye that can be visualized within the surgical suite shown in FIG. 1.
Figure 2B:
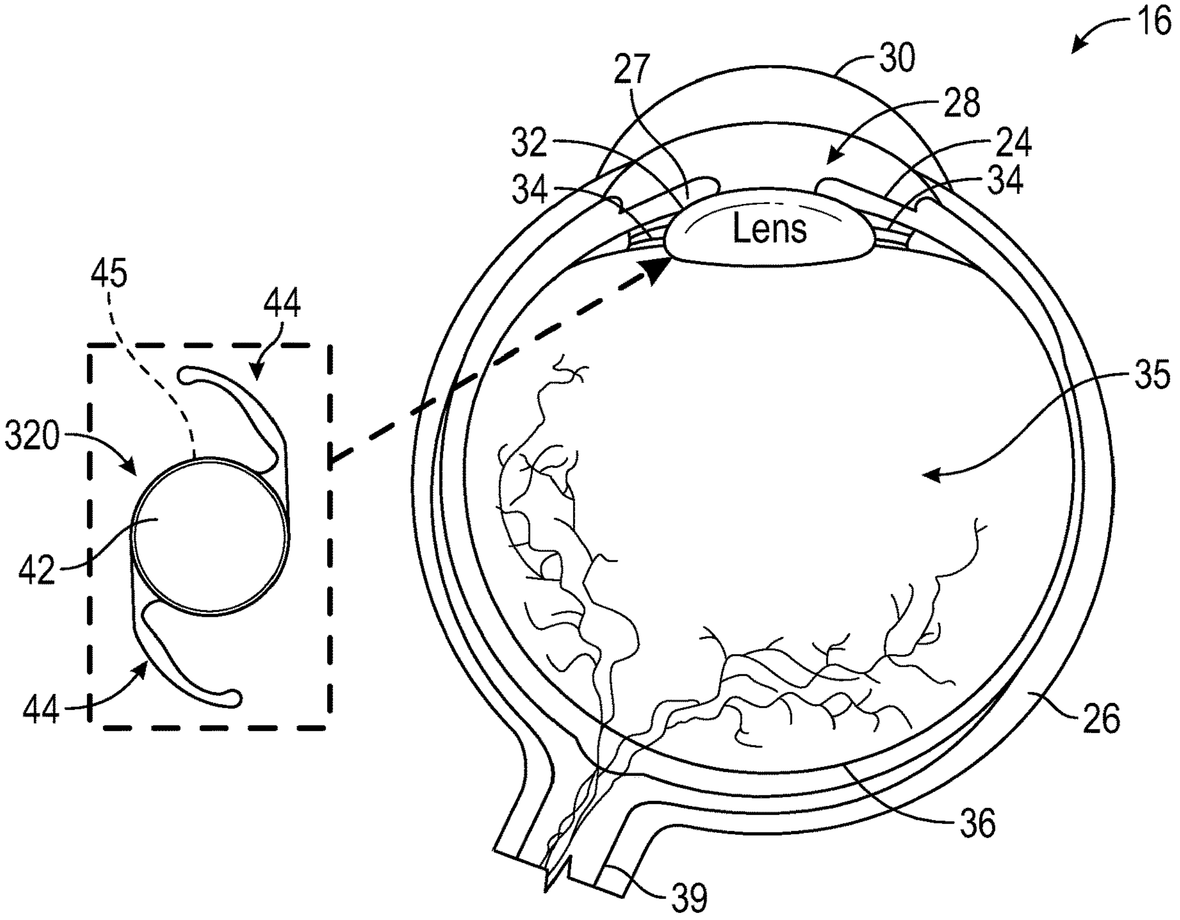
FIG. 2B is a cross-sectional side view illustration of the target eye depicted in FIG. 2B.

Referring briefly to FIGS. 2A and 2B, the target eye 16 includes an iris 27 that is surrounded by sclera 26. A pupil 28 is centrally located within/surrounded by the iris 27. As shown in FIG. 2B, the target eye 16 also includes a cornea 30 spanning and protecting the iris 27 and the pupil 28. Light admitted through the pupil 28 passes through a natural lens 32, which in turn is connected to the surrounding anatomy of the target eye 16 via ciliary muscles 34. Also shown in FIG. 2B is the vitreous cavity 35, which is filled with vitreous humor (not shown), a retina 36 lining posterior portions of the vitreous cavity 35, and the optic nerve 39 disposed at the rear of the vitreous cavity 35 opposite the lens 32.

In executing the above-noted instruction set embodying the method 500 or variations thereof, the ECU 25 of FIG. 1 is rendered operable for assisting in the real-time visualization of the target eye 16. To this end, the visualization system 14 facilitates the automated detection and tracking of a perimeter edge 45 of an intraocular lens (IOL) 320 in an exemplary cataract surgery or a refractive lens exchange (REL). The representative IOL 320 of FIG. 2B may be variously embodied as a monofocal, astigmatism-correcting, extended depth-of-focus, toric, multifocal, or accommodative IOL 320 in different embodiments. Such IOLs 320 include an optic zone 42 configured to focus light admitted through the pupil 28 onto the retina 38. The IOL 320 may also include arms or haptics 44 shaped and sized in a suitable manner for stabilizing and securing the IOL 320 within the target eye 16, as appreciated by those skilled in the art.

Referring once again to FIG. 1, the ECU 25 is configured to identify the perimeter edge 45 of FIG. 2B, or an edge of another subject such as the ILM (not shown). Thereafter, the ECU 25 merges different visible and near infrared (NIR) light spectrums to construct the combined image 22 of the target eye 16, and possibly generates an overlay graphic 450 (see FIG. 4) indicative of the present location of the perimeter edge 45. After this occurs, the display screen 24 is commanded by the ECU 25, e.g., via electronic display control signals (arrow $CC_{24}$), to superimpose and display the overlay graphic 450 on top of the combined image 22.

Although the ECU 25 shown in FIG. 1 is depicted as a unitary box for illustrative clarity and simplicity, the ECU 25 within the scope of the disclosure could include one or more networked devices each with a central processing unit or other processor (P) 52 and sufficient amounts of memory (M) 54, including a non-transitory (e.g., tangible) medium that participates in providing data/instructions that may be read by the processor(s) 52. Instructions embodying an edge detection algorithm 55 may be stored in the memory 54 and executed by the processor 52 to perform the various functions described herein, thus enabling the present method 500 exemplified in FIG. 5.

The memory 54 may take many forms, including but not limited to non-volatile media and volatile media. Non-volatile media may include optical and/or magnetic disks or other persistent memory, while volatile media may include dynamic random-access memory (DRAM), static RAM (SRAM), etc., any or all which may constitute a main memory of the ECU 25. Input/output (I/O) circuitry 56 may be used to facilitate connection to and communication with the various peripheral devices used during the ophthalmic procedure, inclusive of the various hardware of the visualization system 14 of FIG. 1.

Other hardware not depicted but commonly used in the art may be included as part of the ECU 25, including but not limited to a local oscillator or high-speed clock, signal buffers, filters, etc. A human machine interface (HMI) 15 may be included within the structure of the visualization system 14 to allow the surgeon to interact with the ECU 25, e.g., via input signals (arrow $CC_{25}$). The ECU 25 may also control the ophthalmic microscope 20 directly, e.g., via microscope control signals (arrow $CC_{20}$), or via the input signals (arrow $CC_{25}$) in different embodiments. Various implementations of the HMI 15 may be used within the scope of the present disclosure, including but not limited to a footswitch, a touch screen, buttons, control knobs, a speaker for voice activation, etc. The ECU 25 of FIG. 1 may be configured to communicate via a network (not shown), for instance a serial bus, a local area network, a controller area network, a controller area network with flexible data rate, or via Ethernet, Wi-Fi, Bluetooth™, near-field communication, and/or other forms of wired or wireless data connection.

Still referring to FIG. 1, the visualization system 14 contemplated herein includes a first camera 60, labeled CAMERA (VIS) for clarity, and a second camera (CAMERA (NIR)) 62. The respective first and second cameras 60 and 62 are configured to detect light in a specific portion of the electromagnetic spectrum. In particular, the first camera 60 is configured or "tuned" to detect incident reflected light 65R in the human-visible spectrum, which is typically defined as corresponding to wavelengths of about 380 nanometers (nm) to about 750 nm. The second camera 62 for its part is configured to detect reflected light 67R in the NIR range, which is typically defined for the purposes of executing the present strategy as "eye-safe" wavelengths of about 780 nm to about 1.4 micrometers (μm).

In a possible construction, the first and second cameras 60 and 62 may be embodied as complementary metal-oxide-semiconductor (CMOS) image sensors, e.g., commercially available CMOS imagers from Teledyne Technologies of Thousand Oaks, CA. As recognized herein, if one were to attempt to use a single CMOS imager to simultaneously detect both visible and NIR light, the resulting images will be suboptimal at least in terms of their sharpness or color. The suboptimal images result from CMOS imagers having a wide sensitivity spectrum. Focusing NIR light and visible light independently of each other, as set forth herein, thus ensures optimal sharpness and color over both of the relevant spectral ranges.

The visualization system 14 illustrated in FIG. 1 also includes a first light source 65 and a second light source 67, with the labels "V" and "NIR" respectively corresponding to visible and NIR light. That is, the first and second light sources 65 and 67 are configured to emit light toward the target eye 16 in a designated portion of the electromagnetic spectrum. Specifically, the first (visible) light source 65 emits visible light 65L, i.e., human-visible light. The second light source 67 separately emits NIR light 67L. The visualization system 14 therefore employs the first and second light sources 65 and 67 as spectrum-specific light sources, and similarly employs the first and second cameras 60 and 62 as spectrum-specific imagers within the scope of the present disclosure.

Various solutions may be used to implement the respective first and second light sources 65 and 67. For instance, the first light source 65 used to generate the visible light 65L may include a red (R) laser diode, a green (G) laser diode, and a blue (B) laser diode, e.g., as an RGB laser diode array configured to generate the visible light 65L as white light. Commercially-available, highly compact RGB laser modules may be used for this purpose, e.g., the Veglas™ RGB laser module from ams OSRAM AG. Similarly, the NIR light source 67 could be embodied as one or more commercially-available NIR laser diodes.

During the illustrated surgical procedure, the visible and near-IR light 65L and 67L reflect off of the target eye 16 at an angle θ. The reflected visible and NIR light 65R and 67R is directed along an optical axis AA extending along an axis of the pupil 28 of FIG. 2A and a suitable optical target ("Target") 61. The optical target 61 may be static, or the optical target 61 may have one or more parameters, e.g., size, font, appearance, etc., that the ECU 25 may adjust via target control signals (arrow $CC_{61}$). The reflected NIR light 67R thereafter reflects off of a hot mirror 68, which as appreciated in the art is typically embodied as a dielectric mirror and dichroic filter, while also allowing the reflected visible light 65R to pass therethrough. The hot mirror 68 may be arranged at about 45° to the second camera 62 as shown, such that the paths of the reflected visible light 65R and the reflected NIR light 67R are orthogonally arranged (90°) with respect to each other.

The reflected NIR light 67R is thus directed toward the second camera 62, possibly passing through a focusing lens 74. The reflected visible light 65R passes through the hot mirror 68 along the optical axis AA in this embodiment, whereupon the reflected visible light 65R falls incident upon the first camera 60 described above. The respective first and second cameras 60 and 62 thereafter output corresponding visible and IR images 71 and 73 to the ECU 25 for further processing.

Figure 3:
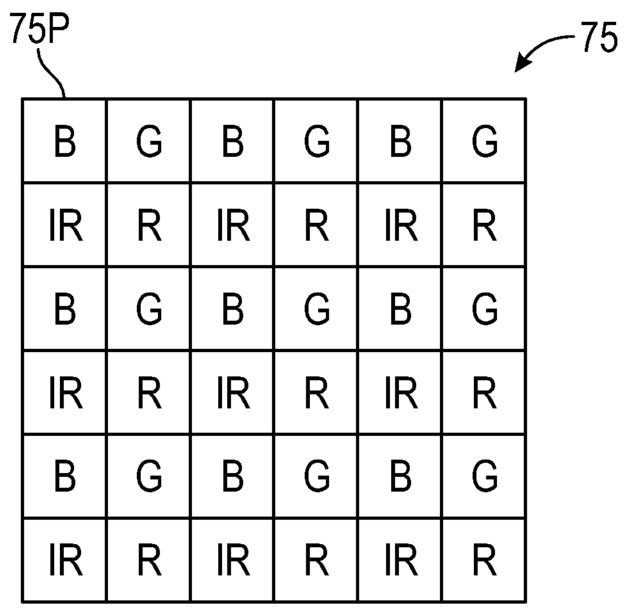
FIG. 3 is a representative combined visible and infrared pixel grid illustrating a possible implementation of the present teachings.

Referring to FIG. 3, a representative pixel grid 75 indicative of a simplified version of the combined image 22 (FIGS. 1 and 4) includes multiple rows and columns of digital pixels 75P. Each constituent digital pixel 75P in turn corresponds to a particular region of the imaged spectrum, i.e., red (R) light, green (G) light, blue (B) light, or infrared (IR), in this instance NIR.

As noted above, a fundamental principle of operation of the present disclosure is to provide a surgeon with an improved view of the IOL 320 (FIGS. 2B and 4), and possibly other difficult to visualize anatomy or eye conditions. This goal is accomplished by combining the visible and NIR images 71 and 73 of FIG. 1 when imaging the target eye 16. That is, the different wavelength spectrums are focused independently as shown in FIG. 1 onto separate, purposefully configured photo receptors, i.e., the first and second cameras 60 and 62. After the visible and NIR images 71 and 73 are collected from the first and second cameras 60 and 62, the ECU 25 executes the edge detection algorithm 55 to detect, isolate, and track the perimeter edge 45 represented in FIGS. 2B and 4. The ECU 25 then merges this information with the visible images 71 from the first camera 60 to construct the combined image 22 of the target eye 16.

Several approaches may be used to produce the combined image 22 of FIG. 1, including the representative combined image 22 of FIG. 4 described below. For instance, the ECU 25 may integrate the NIR pixels and the color/RGB pixels. Here, some of the pixels 75P of FIG. 3 that would ordinarily correspond to a green (G) pixel in a Standard Bayer RGB color filter array (CFA) are replaced with IR pixels to form the combined image 22. The ECU 25 may display the combined image 22 via the display screen(s) 24 as shown in FIG. 1, with the perimeter edge 45 of the IOL 320 of FIG. 2B possibly being represented in the combined image after first being detected from the IR pixels using the edge detection logic 55.

As part of the disclosed approach, one may first transfer one or more RGB images into grayscale images before identifying an edge for the purpose of identifying a red reflex region. An approach such as Hough circle detection may be used to identify a best region of interest (ROI) of the red reflex. Within the identified ROI, the ECU 25 could identify the reflection pixels having the highest blue channel signals. As appreciated in the art, these pixels contain red reflex and reflection of light source. Thus, one or more embodiments of the present method could substitute these identified pixels with a mean ROI intensity to help compensate for hidden red reflex. After substituting those pixels, the ECU 25 can calculated red channel intensity to help quantify red reflex.

Figure 4:
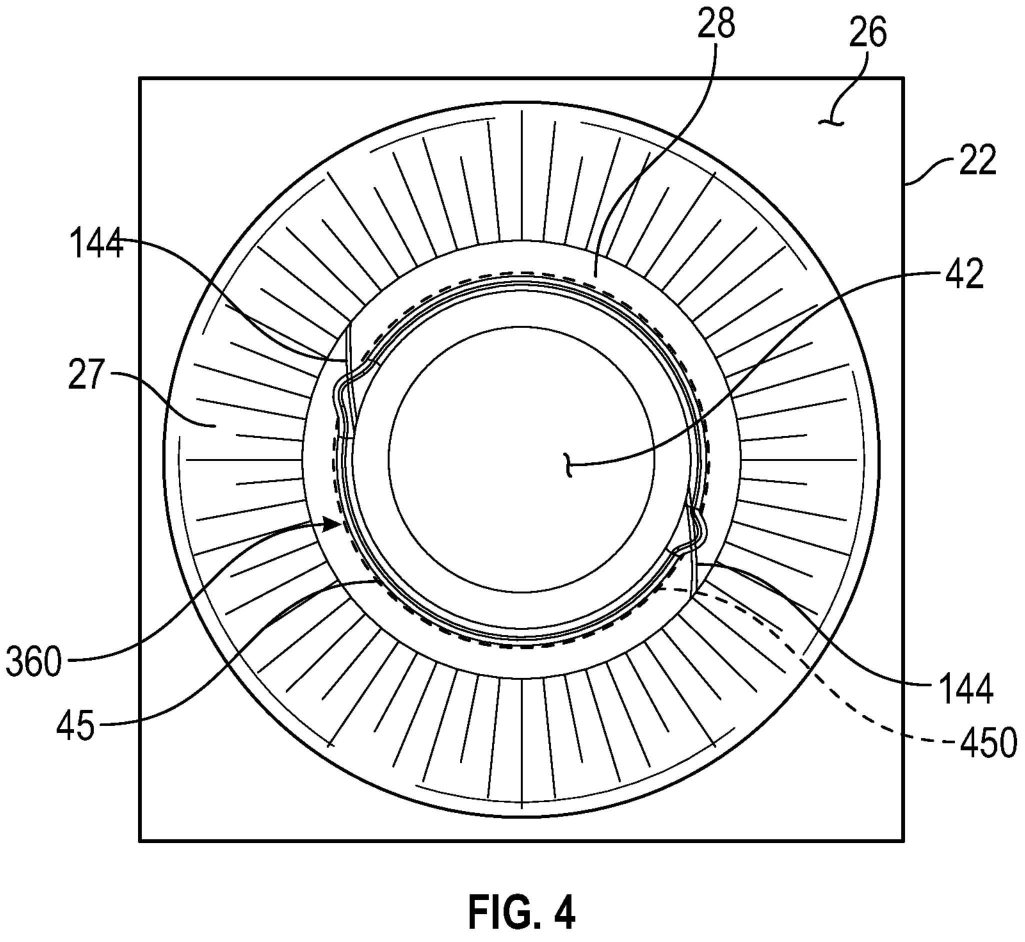
FIG. 4 is a front view illustration of the target eye of FIG. 2B with an overlay graphic depicted thereon to indicate a perimeter edge of an IOL.

As shown in FIG. 4, the combined image 22 is shown of the target eye 16 of FIG. 1 after placement therein of the IOL 360. That is, the IOL 360 is centrally disposed relative to the iris 27 and pupil 28, with portions of the sclera 26 possibly in view within the combined image 22. Haptics 144 are similarly visible at the outer periphery of the optic zone 42 of the implanted IOL 360. Due to its transparency and relatively small size, the IOL 360 is exemplary of the type of device or anatomy that can be difficult to discern with the naked eye, or even under high magnification. By detecting the perimeter edge 45 in the NIR images 73 of FIG. 1 and thereafter combining the visible and IR pixels 75P of FIG. 3, the surgeon is afforded an improved view of the IOL 360.

To further assist the surgeon in visualizing the IOL 360, the ECU 25 in one or more embodiments could output an overlay graphic 450, e.g., a 2D or 3D trace, curve, shape, or other suitable indicator of the location of the perimeter edge 45. The overlay graphic 450 may be superimposed on the combined image 22 as shown. Should the patient 18 of FIG. 1 happen to move the target eye 16 during the course of the procedure, programmed eye tracking capabilities of the visualization system 14 would ensure that the overlay graphic 450 follows the movements of the perimeter edge 45, i.e., with the overlay graphic 450 remaining superimposed over the perimeter edge 45.

Figure 5:
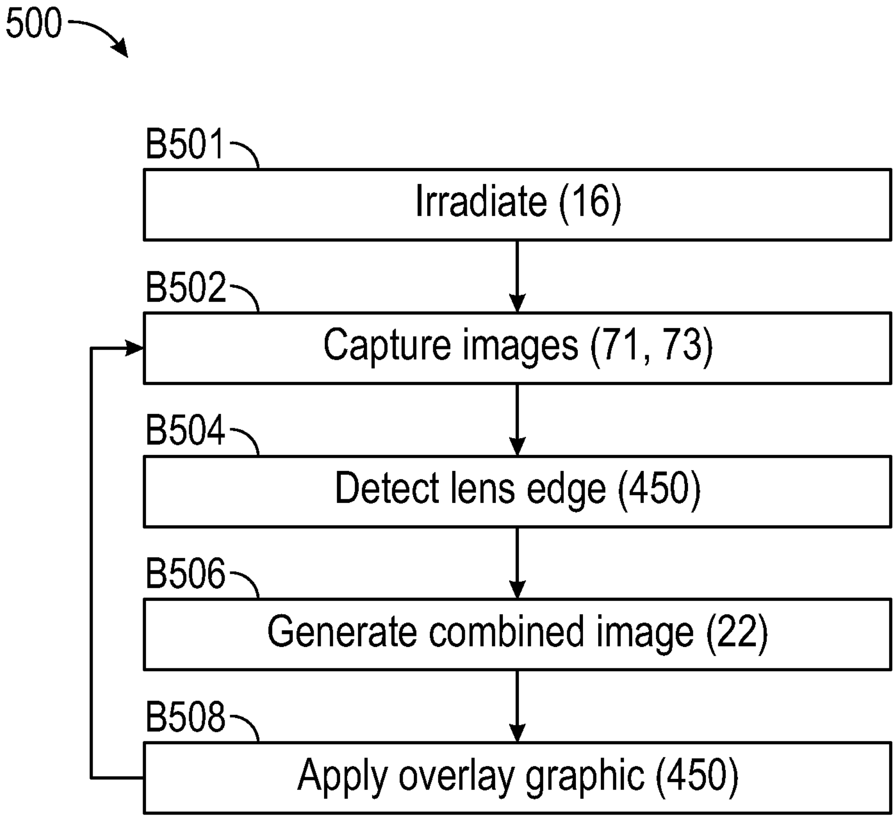
FIG. 5 is a flow chart describing an embodiment of a method for detecting a lens edge in images of the target eye of FIGS. 2A and 2B using the visualization system of FIG. 1.

Referring to FIG. 5, the method 500 may be performed by the ECU 25 of FIG. 1 as series of steps or "logic blocks", each of which is executable by the processor(s) 52 of the ECU 25. The method 500 according to the non-limiting exemplary embodiment of FIG. 5 commences with block B501 ("Irradiate (16)") with irradiation of the target eye 16 with the visible and NIR light 65L and 67L from the respective first and second light sources 65 and 67, as depicted in FIG. 1. As this process occurs, the patient 18 should continue to focus on the optical target 61. The method 500 proceeds to block B502 as the respective visible and NIR light 65L and 67L falls incident upon the target eye 16.

At block B502 ("Capture images (71, 73)"), the first and second cameras 60 and 62 of FIG. 1 receive the reflected visible and NIR light 65R and 67R. In response, the first camera 60 outputs the visible images 71. In a similar manner, the second camera 62 output the NIR images 73. The method 500 proceeds to block B504 once the ECU 25 has received the visible and NIR images 71 and 73, or has begun to receive a stream of such images according to a calibrated sampling frequency.

Block B504 ("Detect lens edge (450)") of the method 500 includes using the edge detection logic 55 of the ECU 25 to detect the perimeter edge 45 of the IOL 320 of FIGS. 2B and 4. The edge detection process occurs herein primarily or possibly exclusively in the NIR spectrum. Edge detection in accordance with block B504 may include determining coordinates in a suitable frame of reference, e.g., an XYZ Cartesian coordinate system, of points in free space corresponding to the detected perimeter edge 45. As the perimeter edge 45 will move with movement of the IOL 360 or of the target eye 16, the edge detection process of block B504 is ongoing through the procedure unless discontinued by the surgeon.

As appreciated in the art, various edge detection algorithms or image processing/computer vision software routines could be run by the ECU 25 for this purpose. By way of example and not of limitation, the ECU 25 could utilize a neural network or programmed logic to recognize patterns in the NIR images 73 representative of the perimeter edge 45. Alternatively, the ECU 25 could execute the Marr-Hildreth algorithm, or could calculate gradients in first and second order derivatives, etc. The method 500 proceeds to block B506 once the ECU 25 has detected and is actively tracking the location of the perimeter edge 45.

Block B506 ("Generate combined image (22)") entails combining the previously collected visible and NIR images 71 and 73 into the combined image 22, e.g., as represented by the pixel grid 75 of FIG. 3 and exemplified in FIG. 4. The method 500 proceeds to block B508 once the ECU 25 has constructed the combined image 22. As with block B504, the performance of block B506 may be performed continuously or at a calibrated rate throughout the process unless otherwise preempted by the surgeon, e.g., via the signals (arrow $CC_{25}$) from the HMI 15 of FIG. 1, which is operable for transmitting the signals (arrow $CC_{25}$) as control commands. The method 500 proceeds to block B508 once the ECU 25 has constructed the combined image(s) 22.

Block B508 ("Apply overlay graphic (450)") of FIG. 5 includes generating and superimposing the overlay graphic 450 on the combined image 22, a simplified example of which is shown in FIG. 4 This control action could include displaying a color image of the target eye 16 on the display screen 24 of FIG. 1, similar to the depiction in FIG. 4, or inside of left and right optical pieces (not shown) of the ophthalmic microscope 20 of FIG. 1 as a backdrop. The control actions of block B508 could include superimposing a 2D or 3D traces over the perimeter edge 45 detected in block B504. The method 500 thereafter returns to block B502, such that blocks B502, B504, B506, and B508 are performed in a loop during the course of the eye procedure.

As appreciated in the art, the surgeon may wish to selectively turn any of the features of blocks B502-B508 on or off as needed. As an example, the surgeon may not always require the combined image 22 or overlay graphic 450, in which case the surgeon could temporarily deactivate the second camera 62 of FIG. 1 and the associated overlay graphic 450 generating features described above. The HMI 15 shown in FIG. 1 could be used for this purpose. Likewise, the surgeon may not always wish to shine bright visible light into the target eye 16, e.g., due to the age or photosensitivity of the patient 18. In this case, the surgeon could decide to temporarily deactivate the first light source 65, i.e., the visible light source. The described method 500 in its various possible embodiments could therefore permit the use of lower light levels, as a bright red reflex light source would not be required. The present teachings have the potential to similarly benefit vitreoretinal surgeries. For instance, by reducing the chances of phototoxicity, the patient 18 would have an easier time looking at the optical target 61 of FIG. 1, and the pupils 28 (FIGS. 2A, 2B, and 4) can naturally dilate without the use of dilation drugs and possible complications sometimes associated therewith.

Embodiments shown in the drawings or the characteristics of various embodiments mentioned in the present description are not necessarily to be understood as embodiments independent of each other. It is possible each of the characteristics described in one of the examples of an embodiment can be combined with one or a plurality of other desired characteristics from other embodiments, resulting in other embodiments not described in words or by reference to the drawings. Accordingly, such other embodiments fall within the framework of the scope of the appended claims. The detailed description and the drawings are supportive and descriptive of the disclosure, but the scope of the disclosure is defined solely by the claims. While some embodiments for carrying out the claimed disclosure have been described in detail, various alternative designs and embodiments exist for practicing the disclosure defined in the appended claims.

The invention claimed is:

1. A visualization system for use during an ophthalmic procedure on a target eye, comprising:

- a first light source operable for directing visible light toward the target eye, the first light source including an array of red, green, and blue (RGB) laser diodes;
- a second light source operable for directing near infrared (NIR) light toward the target eye, the second light source including at least one NIR laser diode;
- a hot mirror configured to direct reflected light from the target eye along two paths, including a visible light path and an NIR light path, wherein the reflected light includes reflected visible light and reflected NIR light;
- a first complementary metal-oxide-semiconductor (CMOS) image sensor positioned in the visible light path, and configured to detect the reflected visible light and output a visible image comprised of RGB pixels;
- a second CMOS image sensor positioned in the NIR light path, and configured to detect the reflected NIR light and output an NIR image comprised of NIR pixels; and
- an electronic control unit (ECU) programmed to detect a perimeter edge of an intraocular lens (IOL) in the NIR image using edge detection logic, merge the visible image with the NIR image to construct a combined image, and apply an overlay graphic onto the combined image to indicate the perimeter edge of the IOL.

2. The visualization system of claim 1, further comprising:

- a display screen in communication with the ECU, and operable for displaying the overlay graphic on the combined image.

3. The visualization system of claim 1, further comprising:

- a human machine interface in communication with the ECU, wherein the human machine interface is operable for transmitting control commands to the ECU to thereby change a control setting of the first light source.

4. The visualization system of claim 1, wherein the edge detection logic includes a neural network and/or a Marr-Hildreth algorithm.

5. A visualization system for use during an ophthalmic procedure on a target eye, comprising:

- a first light source operable for directing visible light toward the target eye;
- a second light source operable for directing near infrared (NIR) light toward the target eye;
- a hot mirror configured to direct reflected light from the target eye along two paths, including a visible light path and an NIR light path, wherein the reflected light includes reflected visible light and reflected NIR light;
- a first camera positioned in the visible light path, and configured to detect the reflected visible light and output a visible image;
- a second camera positioned in the NIR light path configured to detect the reflected NIR light and output an NIR image; and an electronic control unit (ECU) programmed to detect a perimeter edge of an imaged portion of the target eye in the NIR image using edge detection logic, merge the visible image with the NIR image to construct a combined image, and indicate the perimeter edge in the combined image.

6. The visualization system of claim 5, further comprising:

a display screen in communication with the ECU, and operable for displaying an overlay graphic on the combined image, wherein the overlay graphic is indicative of a location of the perimeter edge.

7. The visualization system of claim 5, wherein the first camera and the second camera include complementary metal-oxide-semiconductor (CMOS) image sensors.

8. The visualization system of claim 5, wherein the ophthalmic procedure includes a lens replacement surgery in which an intraocular lens (IOL) is inserted into the target eye, and wherein the imaged portion of the target eye includes the IOL.

9. The visualization system of claim 5, further comprising a human machine interface in communication with the ECU, wherein the human machine interface is operable for transmitting control commands to the ECU to thereby change a control setting of the first light source.

10. The visualization system of claim 5, wherein the edge detection logic includes a neural network.

11. The visualization system of claim 5, wherein the edge detection logic includes a Marr-Hildreth algorithm.

12. The visualization system of claim 5, wherein the visible light path and the NIR light path are arranged orthogonally with each other.

13. A method for use during an ophthalmic procedure on a target eye, the method comprising:

directing visible light from a first light source toward the target eye;

directing near infrared (NIR) light from a second light source toward the target eye;

directing reflected visible light and reflected NIR light from the target eye along a visible light path and an NIR light path, respectively, using a hot mirror;

detecting the reflected visible light via a first camera positioned in the visible light path, and outputting a visible image in response thereto;

detecting the reflected NIR light via a second camera positioned in the NIR light path, and outputting an NIR image in response thereto;

detecting, via an electronic control unit (ECU), a perimeter edge of an imaged portion of the target eye in the NIR image using edge detection logic;

merging the visible image with the NIR image to construct a combined image;

and indicating the perimeter edge in the combined image.

14. The method of claim 13, wherein indicating the perimeter edge in the combined image includes displaying an overlay graphic on the combined image via a display screen in communication with the ECU, wherein the overlay graphic is indicative of a location of the perimeter edge.

15. The method of claim 13, wherein detecting the reflected visible light via a first camera and detecting the reflected NIR light via the second camera includes using one or more complementary metal-oxide-semiconductor (CMOS) image sensors.

16. The method of claim 13, wherein the ophthalmic procedure includes a lens replacement surgery in which an intraocular lens (IOL) is inserted into the target eye, and wherein detecting the perimeter edge of the imaged portion of the target eye in the imaged portion of the target eye includes detecting a perimeter edge of the IOL.

17. The method of claim 13, wherein detecting the perimeter edge of the imaged portion of the target eye includes detecting a perimeter edge of a red reflex of the target eye.

18. The method of claim 13, further comprising transmitting control commands to the ECU via a human machine interface to thereby change a control setting of the first light source during the ophthalmic procedure.

19. The method of claim 13, wherein detecting the perimeter edge of the imaged portion includes using a neural network as at least part of the edge detection logic.

20. The method of claim 13, wherein detecting the perimeter edge of the imaged portion includes using a Marr-Hildreth algorithm as at least part of the edge detection logic.

* * * * *